United States Patent
Blanks et al.

(10) Patent No.: US 9,707,304 B2
(45) Date of Patent: *Jul. 18, 2017

(54) MATERIALS AND METHODS FOR THE TREATMENT OF PATHOLOGICAL NEOVASCULARIZATION IN THE EYE

(71) Applicant: Florida Atlantic University Research Corporation, Boca Raton, FL (US)

(72) Inventors: Janet C. Blanks, Boca Raton, FL (US); Howard M. Prentice, Boca Raton, FL (US); C. Kathleen Dorey, Roanoke, VA (US)

(73) Assignee: FLORIDA ATLANTIC UNIVERSITY RESEARCH CORPORATION, Boca Raton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/970,459

(22) Filed: Dec. 15, 2015

(65) Prior Publication Data

US 2016/0144056 A1 May 26, 2016

Related U.S. Application Data

(63) Continuation of application No. 14/335,254, filed on Jul. 18, 2014, now abandoned, which is a continuation of application No. 13/246,527, filed on Sep. 27, 2011, now Pat. No. 8,785,413.

(60) Provisional application No. 61/386,889, filed on Sep. 27, 2010.

(51) Int. Cl.
| | |
|---|---|
| *A61K 48/00* | (2006.01) |
| *C12N 15/86* | (2006.01) |
| *C12N 5/0793* | (2010.01) |
| *C12N 5/079* | (2010.01) |
| *C12N 15/63* | (2006.01) |
| *A61K 38/39* | (2006.01) |
| *A61K 9/00* | (2006.01) |
| *C07K 14/78* | (2006.01) |
| *C12N 7/00* | (2006.01) |

(52) U.S. Cl.
CPC ........ *A61K 48/0066* (2013.01); *A61K 9/0048* (2013.01); *A61K 38/39* (2013.01); *A61K 48/005* (2013.01); *A61K 48/0058* (2013.01); *C07K 14/78* (2013.01); *C12N 5/062* (2013.01); *C12N 5/0621* (2013.01); *C12N 7/00* (2013.01); *C12N 15/63* (2013.01); *C12N 15/86* (2013.01); *C12N 2710/10041* (2013.01); *C12N 2710/10071* (2013.01); *C12N 2750/14121* (2013.01); *C12N 2750/14143* (2013.01); *C12N 2750/14171* (2013.01); *C12N 2830/002* (2013.01); *C12N 2830/008* (2013.01); *C12N 2830/32* (2013.01)

(58) Field of Classification Search
None
See application file for complete search history.

(56) References Cited

U.S. PATENT DOCUMENTS 8,785,413 B2 * 7/2014 Blanks et al. .............. 514/44 R

OTHER PUBLICATIONS

Dougherty et al. Mole Vision 2008;14:471-80.*
Balaggan et al. Gene Ther 2006;13:1153-65.*
Bainbridge et al. Gene Therapy 2003;10:1049-54.*

* cited by examiner

*Primary Examiner* — Janice Li
(74) *Attorney, Agent, or Firm* — Ferris H. Lander, Inc.

(57) ABSTRACT

The subject invention provides materials and methods useful in safely and effectively preventing pathological proliferation of blood vessels. The prevention of the over-proliferation of blood vessels according to the subject invention is particularly advantageous for treatment of certain ocular conditions including age-related macular degeneration (AMD), retinopathy of prematurity (ROP) and diabetic retinopathy. In preferred embodiments, the subject invention provides materials and methods for effective treatment of pathological ocular neovascularization using gene therapy. In a specific embodiment the materials and methods of the subject invention can be used to treat AMD.

15 Claims, 6 Drawing Sheets

FIG 4A
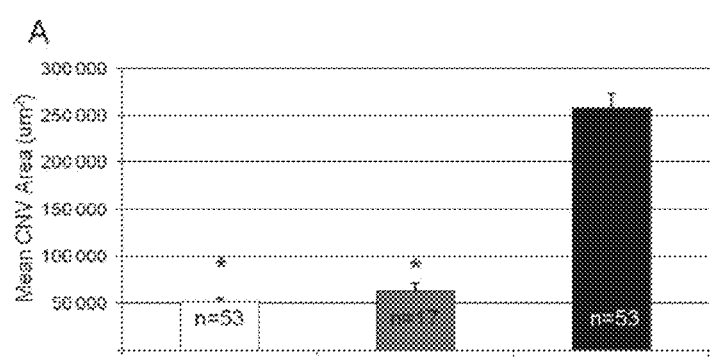
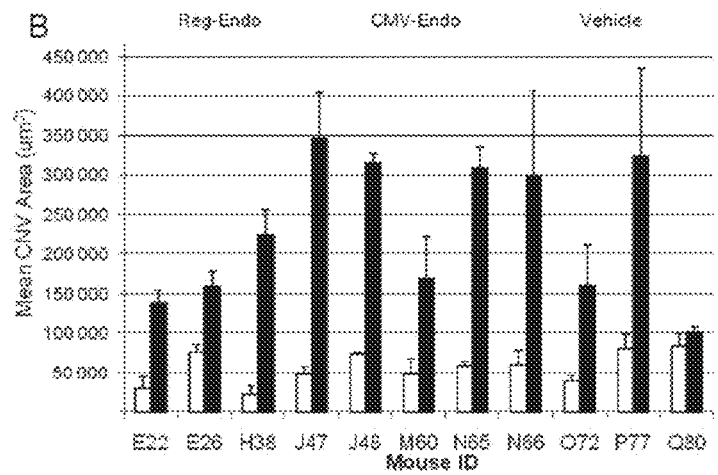
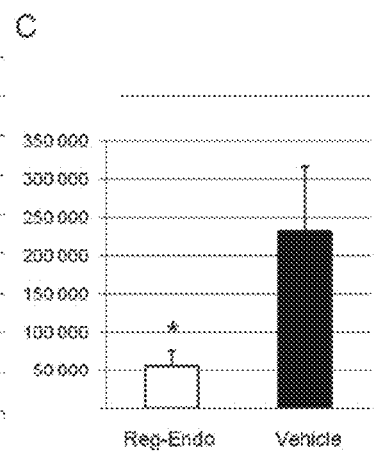
FIG 4B
FIG 4C

MATERIALS AND METHODS FOR THE TREATMENT OF PATHOLOGICAL NEOVASCULARIZATION IN THE EYE

CROSS-REFERENCE TO RELATED APPLICATION

This application is a continuation of U.S. Ser. No. 14/335,254, filed on Jul. 18, 2014, which is a continuation of U.S. Ser. No. 13/246,527, filed on Sep. 27, 2011, now U.S. Pat. No. 8,785,413, which issued on Jul. 22, 2014; and claims the priority benefit of U.S. Provisional Application Ser. No. 61/386,889, filed Sep. 27, 2010, the contents of each of which are incorporated herein by reference in their entirety.

GOVERNMENT SUPPORT

This invention was made with government support under grant/contract number EY016119 awarded by the National Institutes of Health. The government has certain rights in the invention.

SEQUENCE LISTING

This application incorporates by reference in its entirety the Sequence Listing entitled 1087U001CON2SEQLST15DEC2015.txt (1,966 bytes), which was created Dec. 15, 2015 and filed with the application on Dec. 15, 2015.

BACKGROUND OF INVENTION

People suffering from visual impairment face many challenges in performing routine daily activities and/or may not be able to fully enjoy the visual aspects of their surroundings. Of particular concern are visual impairments caused by damage to the retina, which occur in conditions such as age-related macular degeneration (AMD), diabetic retinopathy, and retinopathy of prematurity.

Age-related macular degeneration (AMD) is the leading cause of blindness among adults over the age of 60 in the Western world [Klein, Peto et al., (2004)] with approximately 2 million people suffering from AMD in the US and over 7 million more people at risk (Friedman, O'Colmain et al., 2004). AMD is a multifactorial disease that affects the central (or macular) portion of the retina, the light-sensitive tissue that lines the back of the eye and is responsible for central vision and the detection of fine detail (or acuity).

The acute loss of central vision associated with the wet, or neovascular, form of AMD is the result of unstable, new abnormal blood vessels that grow into the back of the eye where they interfere with normal vision. Prevention of this pathological process, termed choroidal neovascularization, or CNV, is the major target for treatment of the "wet" form of AMD. In AMD patients, CNV is strongly associated with hypoxia and chronic inflammation. These events typically precede CNV, and are thought to play an underlying role in the induction of the neovascular process.

There is a critical need for alternative and more effective treatments for AMD because, for example, the existing treatment requires multiple, costly injections into the eye with the possibility of infection.

Diabetic retinopathy is a progressive disease characterized by abnormalities of the blood vessels of the retina, such as weakening of the blood vessel walls, leakage from the blood vessels, and bleeding and scarring around new vessels. Diabetic retinopathy results in impairment of a person's vision causing severely blurred vision and, potentially, blindness. The World Health Organization indicates that diabetes afflicts 120 million people worldwide, and estimates that this number will increase to 300 million by the year 2025. Diabetic retinopathy is a form of visual impairment often suffered by diabetics.

Due to significant medical advancements, diabetics are able to live much longer than in the past. However, the longer a person has diabetes the greater the chances of developing diabetic retinopathy. Affecting over 5.3 million Americans, diabetic retinopathy is the leading cause of blindness among adults in the United States. Annually, in the United States, between 12,000 and 24,000 people lose their sight because of diabetes.

While management of diabetic retinopathy has improved, risk of complications, such as loss of visual acuity, loss of night vision and loss of peripheral vision, remains significant. Currently, laser photocoagulation is the most effective form of therapy for advanced disease. Unfortunately, current treatment options are inadequate and the disease is often progressive even with successful glucose control.

Retinopathy of prematurity (ROP) is a disorder of retinal blood vessel development in the premature infant. Under normal development, blood vessels grow from the back central part of the eye out toward the edges. In premature babies, this process is not complete and the abnormal growth of the vessels proliferates leading to scar tissue development, retinal detachment and possibly complete blindness.

ROP is the major cause of blindness in children under the age of seven. Improved care in the neonatal intensive care unit has reduced the incidence of retinopathy of prematurity in moderately premature infants. Ironically, however, increasing rates of survival of very premature infants, who would have had little chance of survival in the past, have increased the occurrence of ROP.

Current research shows promise that the prevention of retinal blood vessel damage, which marks retinopathy, may be achieved by the utilization of certain compounds. For example, it has been demonstrated that, in retinal epithelial cells, glutamine deprivation can lead to upregulation of vascular endothelial growth factor (VEGF) expression (Abcouwer S. et al., "Response of VEGF expression to amino acid deprivation and inducers of endoplasmic reticulum stress," *Invest Ophthalmol Vis Sci*, August 2002, pp. 2791-8, Vol. 43, No. 8). Most sick premature infants are deprived of glutamine during the time they receive supplemental oxygen, a known predisposing factor in the development of ROP. The over expression of VEGF during this time period is also thought to be involved in the pathogenesis of ROP.

Endostatin, a 20 kDa proteolytic fragment of the carboxy terminus of collagen XVIII, was discovered in 1997. It was the first endogenous inhibitor of angiogenesis identified as a fragment of a matrix protein. By binding multiple receptors and initiating numerous intracellular pathways, endostatin elicits a broad spectrum of anti-proliferative, anti-migratory, and apoptotic effects on the endothelial cells that line the walls of blood vessels.

Although the delivery of anti-angiogenic agents has been shown to result in the destruction of newly formed blood vessels the constant presence of an anti-angiogenic agent, such as endostatin, may result in long-term deleterious effects on normal vessels in the eye.

BRIEF SUMMARY

The subject invention provides materials and methods useful in safely and effectively preventing or treating pathological proliferation of blood vessels in the eye. The prevention of the over-proliferation of blood vessels according to the subject invention is particularly advantageous for treatment of certain ocular conditions including age-related macular degeneration (AMD), retinopathy of prematurity (ROP) and diabetic retinopathy.

In preferred embodiments, the subject invention provides materials and methods for effective treatment of pathological ocular neovascularization using gene therapy. In a specific embodiment the materials and methods of the subject invention can be used to treat AMD.

Advantageously, the novel gene therapy strategies of the subject invention provide regulated production of an angiogenesis-inhibiting protein, such as endostatin. Specifically, the use of a hypoxia-regulated, retinal pigment epithelial cell-specific vector provides a pathology-initiated regulation of the expression of an angiogenesis inhibitor. The administration of this vector and the subsequent regulated expression of the inhibitor can be used to treat pathological ocular neovascularization, including, for example, the most devastating effects of "wet" AMD.

In accordance with the subject invention, the angiogenesis inhibitor is regulated by a promoter that turns on the gene therapy vector to produce the inhibitor only in pathologic areas of neovascularization. Thus, the production of the inhibitor is regulated, i.e., is not produced all of the time and at all places. The result is a more efficacious delivery of the inhibitor leading to an improved outcome compared to therapies where a medicament is periodically injected into the eye or is constantly released from a gene therapy vector.

An additional advantage of the cell-specific, regulated vector of the subject invention is that the mechanism of action to reduce neovascularization has been established. This facilitates further refinements to the technique to achieve even better results.

The compositions of the subject invention can be formulated according to known methods for preparing pharmaceutically useful compositions. In general, the compositions of the subject invention will be formulated such that an effective amount of the bioactive agent is combined with a suitable carrier in order to facilitate effective administration of the composition.

In accordance with the invention, pharmaceutical compositions comprise an active agent, and one or more non-toxic, pharmaceutically acceptable carriers or diluents. Pharmaceutical carriers or excipients may contain inert ingredients that do not interact with the active agent, or ingredients that do interact with the active agent but not in a fashion so as to interfere with the desired effect. In general, the formulations are prepared by uniformly and intimately bringing into association the active ingredient with a liquid carrier.

BRIEF DESCRIPTION OF THE SEQUENCES

SEQ ID NO:1 is a hypoxia responsive element (HRE) sequence useful according to the subject invention.
SEQ ID NO:2 is a hypoxia responsive element (HRE) sequence useful according to the subject invention.
SEQ ID NO:3 is a neuron restrictive silencer element (NRSE) sequence useful according to the subject invention.
SEQ ID NO:4 is a primer sequence useful according to the subject invention.
SEQ ID NO:5 is a primer sequence useful according to the subject invention.
SEQ ID NO:6 is a primer sequence useful according to the subject invention.
SEQ ID NO:7 is a primer sequence useful according to the subject invention.

BRIEF DESCRIPTION OF DRAWINGS

FIG. 4A shows that the mean CNV area in eyes treated with Regulated Endostatin virus or CMV Endostatin was significantly lower than that of vehicle-treated control eyes. (*P<0.001, t-test; n=# of lesions measured). FIG. 4B shows the mean CNV area of the AAV2-HRSE-HRE-RPE65-Endostatin injected (white bars) and the contralateral, vehicle injected eyes (black bars) from the same mouse. Only mice that had at least 2 countable lesions per eye are shown. FIG. 4C compares mean CNV area in all eyes treated with regulated endostatin with those from the contralateral, vehicle injected eyes (from B). (*P<0.001; paired T-test).

DETAILED DISCLOSURE

Figure 1:
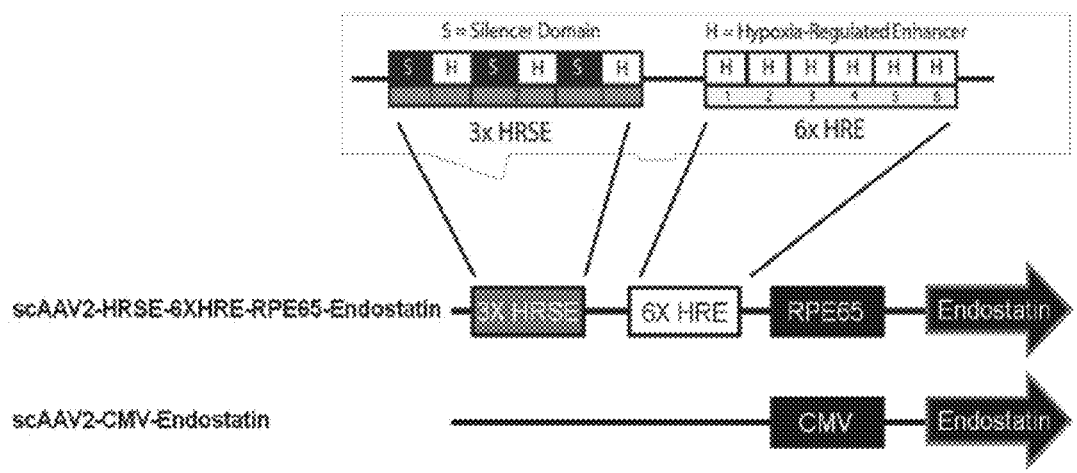
FIG. 1 illustrates the vector design for regulated production of endostatin in hypoxic retinal pigment epithelial (RPE) (scAAV2-HRSE-6XHRE-RPE65-Endostatin) and the constitutive endostatin vector construct (scAAV2-CMV-Endostatin). The regulated endostatin construct contains, in the 5' to 3' direction, a hypoxia-regulated silencing element (HRSE) containing the tandem alternating repeats of 3 copies neuron restrictive silencer element (NRSE) with 3 copies of the HRE-HIF1 enhancer element, 6 tandem copies of the HRE-HIF1 enhancer element, and the RPE promoter.

There is a critical need for new materials and methods for protecting normal retinal tissue from cell damage due to abnormal neovascularization, as well as for retarding further growth of new vessels after neovascularization has already occurred. In one embodiment, the subject invention provides a novel form of gene therapy wherein an anti-angiogenic agent is produced only at the site of abnormal new blood vessels and only under pathological conditions.

In a specific embodiment of the subject invention, gene therapy can be used for preventing the proliferation of abnormal retinal blood vessels in a patient. Specifically, as described herein, the compounds produced by the vector of the subject invention are effective for inhibiting pathological vascular proliferation.

Accordingly, the subject invention is useful prophylactically and therapeutically for treating animals, including humans and other mammals, at risk for pathological vascular proliferation including vascular retinopathy and vasculature associated with tumors. These compositions can be administered to the elderly, premature infants, diabetics, or others who are at risk for retinal disease.

In a preferred embodiment, the method of the subject invention utilizes a gene therapy vector that drives robust protein production in hypoxic retinal pigment epithelial (RPE) cells, but not in normoxic cells. Advantageously, the vector is cell- and tissue-specific since the vector is only expressed in RPE cells.

Endostatin is specifically exemplified herein as an angiogenesis inhibitor. Other angiogenesis inhibitors currently known or that will be developed in the future and can be used. Other known angiogenesis inhibitors include, for example, VEGF receptors, angiostatin, and PF-4.

The RPE-specific gene therapy vector of the subject invention has been found to significantly reduce neovascularization in a laser-induced murine model of choroidal neovascularization (an accepted animal model of AMD). This method provides a unique treatment both prophylactically and after neovascularization is apparent in the early stages of AMD. The gene therapy vector providing regulated production of endostatin can be delivered to AMD patients during the early stages of the disease, which makes this approach relatively inexpensive, more effective and less invasive. In a specific embodiment, the vector can be used to treat the most devastating form of AMD, termed the "Wet" form because it is accompanied by the growth of abnormal blood vessels into the subretinal space, eventually leading to massive photoreceptor cell death in the central, macular region of the retina resulting in blindness.

Hypoxia-Regulated, Tissue-Specific Expression Vector

In one aspect, the subject invention provides an expression vector for prevention and/or treatment of ocular neovascularization as well as diseases associated with ocular neovascularization. In one embodiment, the expression vector comprises a hypoxia-responsive element, an ocular-specific promoter, and a transgene encoding a therapeutic molecule, wherein the transgene is operably linked to the ocular-specific promoter and the transgene is placed under the control of the hypoxia-responsive element. The hypoxia-responsive element upregulates gene expression under hypoxia but not under normoxia. The ocular-specific promoter selectively drives gene expression in the target ocular tissue associated with neovascularization.

Ocular tissue associated with neovascularization include tissues having, or at risk of developing, neovascularization. In one embodiment, the gene therapy is selectively delivered to hypoxic foci in tissues, which foci are predisposed to develop neovascularization. In one embodiment, target ocular tissues at risk of developing neovascularization are tissues under hypoxic conditions, ischemnia, and/or chronic inflammation, which usually precede neovascularization.

The term "hypoxia" or "hypoxic condition," as used herein, refers to a pathological condition in which the oxygen concentration in ocular tissues is less than 10%, 8%, 5%, 3%, 1%, or 0.5% oxygen concentration; as a result, the ocular tissue is deprived of oxygen supply. Under normoxic conditions, the oxygen concentration of ocular tissues is about 20%.

In one embodiment, the hypoxia-responsive element is a Hypoxia Response Element (HRE). HRE binds to a transcription factor-hypoxia-inducible factor-1 (HIF-1), which is a basic helix-loop-helix protein formed by heterodimerization of HIF-1α and HIF-1β. Under normoxic conditions, HIF-1α is rapidly degraded by the proteosome, whereas HIF-1β is unregulated. Under hypoxic conditions, heterodimerization of H1α and HIF-1β occurs; HIF1 heterodimer translocates into the nucleus to bind HREs and upregulate gene expression. Use of a HRE is highly advantageous for selective expression of a transgene in cells and tissues under conditions of hypoxia.

In one embodiment, the hypoxia-responsive element comprises the core consensus sequence for the HRE-(A/G)CGT(G/C)C (SEQ ID NO:1), which occurs in the 5' or 3' flanking sequences of greater than 60 hypoxia-regulated genes identified to date. The inclusion of HRE consensus sequences provides an endogenous, exquisitely sensitive regulatory pathway as a physiologic switch for hypoxia-regulated delivery of a therapeutic gene. In one embodiment, the hypoxia-responsive element comprises SEQ ID NO:2.

In one embodiment, the expression vector comprises multiple (such as 2, 3, 4, 5, 6, 7, 8, 9, or more) copies of the hypoxia-responsive element. The hypoxia-responsive element can be placed upstream or downstream of the promoter sequence. In one embodiment, one or multiple copies of hypoxia-responsive element are placed upstream of the promoter sequence.

In a further embodiment, the expression vector further comprises an aerobic silencer—a regulatory element that silences gene expression under normoxic conditions. As a result, the expression of the transgene is conditionally silenced under aerobic conditions, while is robustly induced under hypoxic conditions. In a specific embodiment, the aerobic silencer is derived from neuron-restrictive silencer element (NRSE).

In one embodiment, the expression vector comprises a hypoxia-regulated silenced element (HRSE) comprising one or more copies (such as 2, 3, 4, 5, 6, 7, 8, 9, or more copies) of the hypoxia-responsive element and/or the aerobic silencer. In another embodiment, copies of the hypoxia-responsive element and the aerobic silencer are placed in alternating tandem order.

The aerobic silencer can be placed upstream or downstream of the promoter sequence, or upstream or downstream of the hypoxia-responsive element. In one embodiment, the aerobic silencer is placed upstream of the promoter sequence and the hypoxia-responsive element. In another embodiment, the aerobic silencer is placed downstream of the promoter sequence and the hypoxia-responsive element.

In another embodiment, the aerobic silencer is placed upstream of the promoter sequence but downstream of the hypoxia-responsive element. In another embodiment, the hypoxia-responsive element is placed upstream of the promoter sequence but downstream of the aerobic silencer.

The ocular-specific promoter can be derived from the promoter region of a gene that is only, or selectively, expressed in the ocular tissue of interest (e.g., at or near the site of pathological neovascularization, under hypoxic conditions, and/or inflammation). The ocular tissues of interest include, for example, retinal cells, retinal epithelial cells, Muller cells, choroid cells, etc.

The term "tissue-specific promoter," as used herein, refers to a promoter sequence that only, or selectively, drives gene expression in the specific tissue type where the gene expression is desired, whereas the promoter sequence does not drive gene expression, or drives expression to a much lesser extent, in other types of tissues. In certain embodiments, the promoter is specific for a certain type of the ocular tissue, such as retinal cells, retinal epithelial cells, Muller cells, choroid cells, etc. For example, a RPE-specific promoter only drives gene expression in RPE cells, and leaving other types of eye tissues unmodified by transgene expression.

In certain embodiments, the ocular-specific promoter can be derived from the promoter sequence of RPE-65, which is selectively expressed in retinal pigment epithelium (RPE) cells; the vitelliform macular dystrophy (VMD2) promoter that is specific for RPE-specific expression; the promoter sequence of BFSP1—an eye lens-specific gene; the promoter sequence of glial fibrilary acidic protein gene (GFAP), which is selectively expressed in Muller cells and retinal glial cells. In another embodiment, the ocular-specific promoter is not the GFAP promoter.

Preferably, the hypoxia-responsive element, the aerobic silencer, and the promoter sequence are of mammalian origin, or more preferably, of human origin. In an alternative embodiment, the promoter, itself, comprises a hypoxia-responsive element and/or aerobic silencer. In an embodiment, the promoter sequence is placed upstream of the transgene.

In certain embodiments, the therapeutic molecule is an angiogenesis inhibitor (also referred to as anti-angiogenic agent). As used herein, the term "angiogenesis" refers to the generation of new blood vessels into a tissue or organ. Under normal physiological conditions, humans or animals undergo angiogenesis only in very specific restricted situations. For example, angiogenesis is normally observed in wound healing, fetal and embryonal development, and formation of the corpus luteum, endometrium and placenta. The term "anti-angiogenic activity" refers to the capability of an agent or composition to inhibit the formation of new blood vessels.

Angiogenesis inhibitors useful according to the subject invention include, but are not limited to, endostatin, fibroblast grow factor (FGF) or VEGF receptors, angiostatin, pigment epithelium-derived factor (PEDF), platelet factor 4 (PF-4), and the amino terminal fragment (ATF) of urokinase containing an elongation factor G (EFG)-like domain. In one embodiment, angiostatin is derived from the amino-terminal fragment of plasinogen, and comprises the anti-angiogenic fragment of angiostatin having kringles 1 to 3. Endostatin is specifically exemplified herein as an angiogenesis inhibitor. In preferred embodiments, the angiogenesis inhibitors, such as endostatin, are of human origin.

Genes encoding other anti-angiogenesis protein can also be used. Such genes include, but are not limited to, genes encoding inhibitors of FGF or VEGF, stroaml derived factor 1 (SDF-1), and metalloproteinase inhibitors such as BB94.

The nucleic acid constructs can be incorporated into vectors suitable for gene therapy. The expression vector of the subject invention can be a plasmid, or preferably a suitable viral vector. Viral vectors useful for performing the subject invention include recombinant adeno-associated virus (rAAV)-based vectors; adenoviral (Ad) vectors; AAV-adenoviral chimeric vectors; retroviral vectors such as lentiviral vectors, human T-cell lymphotrophic viral vectors; and herpes simplex virus (HSV)-based viral vectors. In certain specific embodiments, the expression vector is an adenovirus-based vector, a recombinant adeno-associated virus (rAAV)-based vector, or a lentiviral vector.

Preferred embodiments of the vectors are recombinant adeno-associated virus (rAAV) vectors. In certain specific embodiment, the AAV vectors are selected from AAV1, AAV2, AAV3, AAV5, AAV5, AAV6, or AAV7. In some embodiments optimized for efficient transduction of retinal cells and rapid onset of expression, the strain rAAV 2/1 is preferred.

In a specific embodiment, the subject invention provides an AAV vector comprising an endostatin gene, wherein the endostatin gene is operably linked to a RPE65 promoter, and the endostatin gene is placed under the control of HRSE and HRE.

Gene Therapy for Ocular Neovascularization

In another aspect, the subject invention provides a method of prevention and/or treatment of ocular neovascularization as well as diseases associated with ocular neovascularization, via the delivery of the expression vector of the subject invention using gene therapy. In one embodiment, the method comprises administering, into a target ocular tissue of the subject, an expression vector comprising a transgene encoding a therapeutic molecule, wherein the transgene is operably linked to an ocular-specific promoter and is placed under the control of a hypoxia-responsive element, wherein the ocular-specific promoter selectively drives gene expression in the ocular tissue associated with neovascularization, and the hypoxia-responsive element upregulates gene expression under hypoxia but not under nomoxia.

In one embodiment, the expression vector, or a therapeutic composition comprising the expression vector is delivered into, or near, the area of neovascularization, where the pathological proliferation of new blood vessels occur. In another embodiment, the expression vector, or a therapeutic composition comprising the expression vector can also be delivered to a site that is at risk for developing neovascularization.

The term "subject" or "patient," as used herein, describes an organism, including mammals such as primates, to which treatment with the compositions according to the subject invention can be provided. Mammalian species that can benefit from the disclosed methods of treatment include, but are not limited to, apes, chimpanzees, orangutans, humans, monkeys; domesticated animals such as dogs, cats, horses, cattle, pigs, sheep, goats, and chickens; and other animals such as mice, rats, guinea pigs, and hamsters.

In one embodiment, the subject or patient has pathological ocular neovascularization such as chorodial neovascularization, which can be detected using angiography, e.g., fluorescein angiography, alone or in combination with indocyanine-green angiography.

The term "treatment" or any grammatical variation thereof (e.g., treat, treating, and treatment etc.), as used herein, includes but is not limited to, ameliorating or alleviating a symptom of ocular neovascularization, reducing, suppressing, inhibiting, lessening, or affecting the progression, severity, and/or scope of ocular neovascularization.

The term "prevention" or any grammatical variation thereof (e.g., prevent, preventing, and prevention etc.), as used herein, includes but is not limited to, delaying the onset of ocular neovascularization. Prevention, as used herein, does not require the complete absence of symptoms.

As demonstrated herein, the subject invention significantly arrests or retards ocular neoveascularization. Pathological ocular neovascularization that can be prevented and/or treated in accordance with the subject invention can be from any region of the eye. In certain preferred embodiments, the subject invention is used to prevent and/or treat choroidal neovascularization as well as diseases and conditions associated with choroidal neovascularization. Diseases and conditions associated with choroidal neovascularization include, for example, age-related macular degeneration, histoplasmosis, myopic degeneration, choroidal rupture, photocoagulation, choroidal hemangioma, choroidal non-perfusion, choroidal osteomas, choroideremia, retinal detachment, neovascularization at ora serrata, punctate inner choroidopathy, radiation retinopathy, and retinal cryoinjury.

In addition, the subject invention can also be used to prevent and/or treat corneal neovascularization as well as diseases and conditions associated with corneal neovascularization, such as corneal dystrophies. In addition, the subject invention can be used to prevent and/or treat retinal neovascularization as well as diseases and conditions associated with retinal neovascularization including, for example, diabetic retinopathy and retinopathy of prematurity.

Construction of Vectors and Expression Constructs

Vectors useful according to the subject invention can be constructed as described, for example, by Doughetry et al. (Christopher J. Dougherty, George W. Smith, C. Kathleen Dorey, Howard M. Prentice, Keith A. Webster, Janet C. Blanks, "Robust hypoxia-selective regulation of a retinal pigment epithelium-specific adeno-associated virus vector" *Molecular Vision* 14:471-480 (Mar. 7, 2008), which is incorporated herein, in its entirety, by reference.

As used herein, the term "vector" refers to a nucleic acid molecule capable of transporting another nucleic acid. Vectors capable of directing the expression of genes to which they are operatively linked are referred to herein as "expression vectors." In general, expression vectors of utility in recombinant DNA techniques are often in the form of "plasmids," which refer to circular double stranded DNA loops which, in their vector form are not bound to the chromosome.

Vectors may also be viral vectors wherein the viral vector is selected from the group consisting of a lentivirus, adenovirus, adeno-associated virus and virus-like vectors. The vector may also be a lipid vesicle or liposome wherein the DNA is surrounded by a lipid emulsion that is taken up by the cell. The invention is intended to include such other forms of expression vectors which serve equivalent functions and which become known in the art subsequently hereto. An "expression vector" is a vector capable of expressing a DNA (or cDNA) or RNA molecules cloned into the vector and, in certain cases, producing a polypeptide or protein. Appropriate transcriptional and/or translational control sequences are included in the vector to allow it to be expressed in a cell.

As used herein, the term "operably linked" refers to a juxtaposition of the components described wherein the components are in a relationship that permits them to function in their intended manner. In general, operably linked components are in contiguous relation.

Expression constructs of the invention may optionally contain a transcription termination sequence, a translation termination sequence, signal peptide sequence, and/or regulatory elements. Transcription termination regions can typically be obtained from the 3' untranslated region of a eukaryotic or viral gene sequence. Transcription termination sequences can be positioned downstream of a coding sequence to provide for efficient termination. Signal peptides are a group of short amino terminal sequences that encode information responsible for the relocation of an operably linked peptide to a wide range of post-translational cellular destinations, ranging from a specific organelle compartment to sites of protein action and the extracellular environment. Targeting a peptide to an intended cellular and/or extracellular destination through the use of operably linked signal peptide sequence is contemplated for use with the peptides of the invention. Unique restriction enzyme sites can be included at the 5' and 3' ends of the expression construct to allow for insertion into a polynucleotide vector.

Expression of the cloned sequences occurs when the expression vector is introduced into an appropriate host cell. If a eukaryotic expression vector is employed, then the appropriate host cell would be any eukaryotic cell capable of expressing the cloned sequences. Vectors include chemical conjugates such as described in WO 93/04701, which has a targeting moiety (e.g. a ligand to a cellular surface receptor), and a nucleic acid binding moiety (e.g. polylysine), viral vector (e.g. a DNA or RNA viral vector), fusion proteins such as described in PCT/US95/02140 (WO 95/22618) which is a fusion protein containing a target moiety (e.g. an antibody specific for a target cell) and a nucleic acid binding moiety (e.g. a protamine), plasmids, phage etc. The vectors can be chromosomal, non-chromosomal or synthetic.

The vectors can be introduced by standard techniques, e.g., infection, transfection, transduction or transformation. Examples of modes of gene transfer include for example, naked DNA calcium phosphate precipitation, DEAE dextran, electroporation, protoplast fusion, lipofection, cell microinjection and viral vectors.

"Regulatory region" means a nucleic acid sequence which regulates the expression of a second nucleic acid sequence. A regulatory region may include sequences which are naturally responsible for expressing a particular nucleic acid (a homologous region) or may include sequences of a different origin (responsible for expressing different proteins or even synthetic proteins). Regulatory regions include origins of replication, RNA splice sites, enhancers, transcriptional termination sequences, signal sequences which direct the polypeptide into the secretory pathways of the target cell, and promoters.

A regulatory region from a "heterologous source" is a regulatory region that is not naturally associated with the expressed nucleic acid. Included among the heterologous regulatory regions are regulatory regions from a different species, regulatory regions from a different gene, hybrid regulatory sequences, and regulatory sequences which do not occur in nature, but which are constructed by one having ordinary skill in the art.

A "cassette" refers to a segment of DNA that can be inserted into a vector at specific restriction sites. The segment of DNA encodes a polypeptide of interest, and in the case of coding sequences, the cassette and sites of insertion are chosen to ensure insertion of the coding sequences in the proper reading frame for transcription and translation.

Heterologous DNA refers to DNA not naturally located in the cell, or in a chromosomal site of the cell. Preferably, the heterologous DNA includes a gene foreign to the cell.

A "nucleic acid" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semi-synthetic DNA. The sequence of nucleotides or nucleic acid sequence that encodes a protein is called the sense sequence.

A DNA "coding sequence" is a DNA sequence that is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. Alternative 5' terminae are also possible for certain genes. Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. Within the promoter sequence will be found a transcription initiation site (conveniently defined for example, by mapping with nuclease SI), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then optionally trans-RNA spliced and translated into the protein encoded by the coding sequence.

As used herein, the term "downstream," when used in reference to a direction along a nucleotide sequence, means in the direction from the 5' to the 3' end. Similarly, the term "upstream" means in the direction from the 3' to the 5' end.

As used herein, the term "gene" means the gene and all currently known variants thereof and any further variants which may be elucidated.

The therapeutic genes are incorporated into expression vectors, preferably, viral vectors. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector [Kaplitt et al., Molec. Cell. Neurosci. 2:320-330 (1991)], defective herpes virus vector lacking a glycoprotein L gene [Patent Publication RD 371005 A], or other defective herpes virus vectors [International Patent Publication No. WO 94/21807; International Patent Publication No. WO 92/05263]; an attenuated adenovirus vector, such as the vector described by Stratford-Perricaudet et al. [J. Clin. Invest. 90:626-630 (1992); see also La Salle et al., Science 259:988-990 (1993)]; and a defective adeno-associated virus vector [Samulski et al., J. Virol. 61:3096-3101 (1987); Samulski et al., J. Virol. 63:3822-3828 (1989); Lebkowski et al., Mol. Cell. Biol. 8:3988-3996 (1988)].

Adeno-associated viruses (AAV) are small, single-stranded DNA viruses (K. I. Berns, *Parvoviridae: the viruses and their replication*, p. 1007-1041, in F. N. Fields et al., Fundamental Virology, 3rd ed., vol. 2, (Lippencott-Raven Publishers, Philadelphia, Pa.) (1995)). Most serotypes of AAV vectors can be used for gene therapy in the eye (e.g., see Aurricchio et al. 2001 and Yang et al. 2002). Specifically, there are at least eight AAV serotypes with varying degrees of gene transfer efficiencies in vivo and varying unset of efficiencies. The entire sequences of AAV1, 2, 3, 4, 5, 6 have been determined, and the homologies of various serotype genomes are between 52 and 82% (Bantel-Schaal U., and H. zur Hausen. J. Virol. 1999, 73: 939-947, Parvoviridae, Intervirology 5: 83-92)(Bantel-Schaal U., and H. zur Hausen. 1998. Virology 134: 52-63)(Rutledge. E A., C L. Halbert, and D W. Russell. 1998. J. Virol. 72: 309-319). In addition, new AAV serotypes, such as AAV7 and AAV8, etc., have been reported.

The use of vectors derived from the AAVs for transferring genes in vitro and in vivo has been described (see WO 91/18088; WO 93/09239; U.S. Pat. No. 4,797,368, U.S. Pat. No. 5,139,941, EP 488 528). These publications describe various AAV-derived constructs in which the rep and/or cap genes are deleted and replaced by a gene of interest, and the use of these constructs for transferring the said gene of interest in vitro (into cultured cells) or in vivo, (directly into an organism). The replication defective recombinant AAVs according to the invention can be prepared by cotransfecting a plasmid containing the nucleic acid sequence of interest flanked by two AAV inverted terminal repeat (ITR) regions, and a plasmid carrying the AAV encapsidation genes (rep and cap genes), into a cell line which is infected with a human helper virus (for example an adenovirus). The AAV recombinants which are produced are then purified by standard techniques.

The invention contemplates the use of an AAV-derived recombinant virus whose genome encompasses a sequence encoding a nucleic acid encoding a therapeutic transgene (such as an angiogenesis inhibitor) flanked by the AAV ITRs. The invention also relates to a plasmid encompassing a sequence encoding a nucleic acid encoding an anti-angiogenic factor flanked by two ITRs from an AAV. Such a plasmid can be used as it is for transferring the nucleic acid sequence, with the plasmid, where appropriate, being incorporated into a liposomal vector (pseudo-virus).

The general procedures for use of adeno-associated virus (AAV) as a vector for gene therapy are known in the art, such as described in U.S. Pat. Nos. 7,037,713; 6,953,575; 6,897,063; 6,764,845; 6,759,050; 6,710,036; 6,610,290; 6,593,123; 6,582,692; 6,531,456; 6,416,992; 6,207,457; and 6,156,303.

The construction of an AAV vector can be performed using methods known in the art, such as described in Flotte T R. Adeno-associated virus-based gene therapy for inherited disorders. Pediatr Res. 2005 December; 58(6):1143-7; Goncalves M A. Adeno-associated virus: from defective virus to effective vector, Virol J. 2005 May 6; 2:43; Surace E M, Auricchio A. Adeno-associated viral vectors for retinal gene transfer. Prog Retin Eye Res. 2003 November; 22(6): 705-19; Mandel R J, Manfredsson F P, Foust K D, Rising A, Reimsnider S, Nash K, Burger C. Recombinant adeno-associated viral vectors as therapeutic agents to treat neurological disorders. Mol Ther. 2006 March; 13(3):463-83.).

In addition, a reporter gene can be inserted into the vector for the detection of transgene expression. A reporter gene can be detectable by any number of techniques, including by fluorescence detection, calorimetric detection or immunologic detection. Particularly preferred marker genes encode green fluorescent protein and variants thereof.

Purification of recombinant AAV (rAAV) vectors can be accomplished using techniques known in the art, such as heparin sulfate-based columns, which can substantially eliminate adenovirus contamination (Clark et al., 1999; Zolotukhin et al., 1999); U.S. Pat. Nos. 6,143,548 and 6,146,874). Recombinant AAV can also be purified double CsCl banding method (Rolling & Samulski, 1995).

Adenoviruses are eukaryotic DNA viruses that can be modified to efficiently deliver a nucleic acid of the invention to a variety of cell types. Various serotypes of adenovirus exist. Of these serotypes, preference is given, within the scope of the subject invention, to using type 2 or type 5 human adenoviruses (Ad 2 or Ad 5) or adenoviruses of animal origin (see WO94/26914). Those adenoviruses of animal origin which can be used within the scope of the subject invention include adenoviruses of canine, bovine, murine (example: Mavl, Beard 75 (1990) 81), ovine, porcine, avian, and simian (example: SAV) origin. The adenovirus of animal origin is a canine adenovirus, more preferably a CAV2 adenovirus (e.g., Manhattan or A26/61 strain (ATCC VR-800), for example).

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (WO95/02697), the E2 region (WO94/28938), the E4 region (WO94/28152, WO94/12649 and WO95/02697), or in any of the late genes L1-L5.

The replication defective recombinant adenoviruses according to the invention can be prepared by any technique known to the person skilled in the art (Levrero et al., Gene 101 (1991) 195, EP 185 573; Graham, EMBO J. 3 (1984) 2917). In particular, they can be prepared by homologous recombination between an adenovirus or modified adenovirus genome and a plasmid which carries, inter alia, the DNA sequence of interest. Recombinant adenoviruses are recovered and purified using standard molecular biological techniques, which are well known to one of ordinary skill in the art.

In another embodiment, the gene can be introduced in a retroviral vector, e.g., as described in U.S. Pat. No. 5,399,346; Mann et al., 1983, Cell 33:153; U.S. Pat. No. 4,650,764; U.S. Pat. No. 4,980,289; Markowitz et al., 1988, J. Virol. 62:1120; U.S. Pat. No. 5,124,263; EP 453242, EP178220; Bernstein et al. Genet. Eng. 7 (1985) 235; McCormick, BioTechnology 3 (1985) 689; International Patent Publication No. WO 95/07358, published Mar. 16, 1995, by Webster, K. A., Kubasiak, L. A., Prentice, H. and Bishopric, N. H.: Stable germline transmission of a hypoxia-activated molecular gene switch. From the double helix to molecular medicine, (ed. W. J. Whelan et al.), Oxford University Press, (2003); and Kuo et al., 1993, Blood 82:845.

The retroviruses are integrating viruses that infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are disclosed in WO95/02697.

Retroviral vectors can be constructed to function as infectious particles or to undergo a single round of transfection. In the former case, the virus is modified to retain all of its genes except for those responsible for oncogenic transformation properties, and to express the heterologous gene. Non-infectious viral vectors are prepared to destroy the viral packaging signal, but retain the structural genes required to package the co-introduced virus engineered to contain the heterologous gene and the packaging signals. Thus, the viral particles that are produced are not capable of producing additional virus. Targeted gene delivery is described in International Patent Publication WO 95/28494, published October 1995.

Lentiviruses include members of the bovine lentivirus group, equine lentivirus group, feline lentivirus group, ovinecaprine lentivirus group and primate lentivirus group. The development of lentiviral vectors for gene therapy has been reviewed in Klimatcheva et al., 1999, Frontiers in Bioscience 4: 481-496. The design and use of lentiviral vectors suitable for gene therapy is described, for example, in U.S. Pat. No. 6,207,455, issued Mar. 27, 2001, and U.S. Pat. No. 6,165,782, issued Dec. 26, 2000. Examples of lentiviruses include, but are not limited to, HIV-1, HIV-2, HIV-1/HIV-2 pseudotype, HIV-1/SIV, FIV, caprine arthritis encephalitis virus (CAEV), equine infectious anemia virus and bovine immunodeficiency virus. HIV-1 is preferred.

Host cells can be infected with the subject viral vectors ex vivo or in vivo. Suitable host cells infected with the viral vectors include cultured cell lines and cells isolated from living organisms. Preferably, host cells of the subject invention are animal cells, more preferably mammalian cells. Exemplified mammalian host cells include, but are not limited to, cells derived from apes, chimpanzees, orangutans, humans, monkeys, dogs, cats, horses, cattle, pigs, rabbits, sheep, goats, chickens, mice, rats, guinea pigs, and hamsters.

Alternatively, the vector can be introduced in vivo as nucleic acid free of transfecting excipients, or with transfection facilitating agents, e.g., lipofection. The use of cationic lipids may promote encapsulation of negatively charged nucleic acids, and also promote fusion with negatively charged cell membranes [Feigner and Ringold, Science 337:387-388 (1989)].

Particularly useful lipid compounds and compositions for transfer of nucleic acids are described in International Patent Publications WO95/18863 and WO96/17823, and in U.S. Pat. No. 5,459,127. The use of lipofection to introduce exogenous genes into the specific organs in vivo has certain practical advantages. Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (see International Patent Publication WO95/21931), peptides derived from DNA binding proteins (see International Patent Publication WO96/25508), or a cationic polymer (see International Patent Publication WO95/21931).

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter [see, e.g., Wu et al., J. Biol. Chem. 267:963-967 (1992); Wu and Wu, J. Biol. Chem. 263:14621-14624 (1988); Williams et al., Proc. Natl. Acad. Sci. USA 88:2726-2730 (1991)]. Receptor-mediated DNA delivery approaches can also be used [Curiel et al., Hum. Gene Ther. 3:147-154 (1992); Wu and Wu, J. Biol. Chem. 262:4429-4432 (1987)].

Formulations and Administration

The expression vectors and therapeutic composition comprising the expression vectors is administered in an effective amount i.e. an amount sufficient to evoke the desired pharmacological response. This is generally an amount sufficient to produce lessening of one or more of the effects of a pathological vascular proliferation. In the case of retinopathy, it is an amount sufficient to produce regression and/or inhibition of neovascularization and/or an amount sufficient to produce improved visual acuity.

In preferred embodiments, the vectors and therapeutic compositions of the subject invention are administered to a subject by injection into the targeted region of the eye. The amount of vector to be delivered depends on the size of the eye, how extensive an area was being targeted and is readily determined by a practioner. When administered it is preferred that the vectors be given in a pharmaceutical vehicle suitable for injection such as a sterile aqueous solution or dispersion. Following administration, the subject is monitored to detect changes in gene expression. Dose and duration of treatment can be determined individually depending on the condition or disease to be treated. A wide variety of conditions or diseases can be treated based on the gene expression produced by administration of the gene of interest in the vector of the subject invention. The dosage of vector delivered using the method of the invention may vary, depending on the desired response by the host and the vector used. Generally, it is expected that up to 100-200 μg of DNA or RNA can be administered in a single dosage, although a range of 0.5 mg/kg body weight to 50 mg/kg body weight may be suitable for most applications.

In one embodiment, the subject invention utilizes injection techniques require puncturing layers of the eye, including the sclera, choroid, retina, subretina, etc. In one embodiment, to minimize trauma to those layers of the eye, the vectors and therapeutic compositions of the subject invention can be administered into the sub-tenon (i.e., episcleral) space surrounding the scleral portion of the eye. The vectors and therapeutic compositions can also be administered to other regions of the ocular apparatus such as, for instance, the ocular muscles, the orbital fascia, the eye lid, the lacrimal apparatus, and the like as is appropriate.

Preferably, the therapeutic factor or nucleic acid sequence encoding the therapeutic factor is administered via an ophthalmologic instrument for delivery to a specific region of an eye. The use of a specialized ophthalmologic instrument ensures precise administration of the therapeutic factor or the nucleic acid sequence encoding the therapeutic factor, while minimizing damage to adjacent ocular tissue. Delivery of the therapeutic factor or nucleic acid sequence encoding the therapeutic factor to a specific region of the eye also limits exposure of unaffected cells to the therapeutic factor, thereby reducing the risk of side effects. A preferred ophthalmologic instrument is a combination of forceps and subretinal needle or sharp bent cannula.

In certain embodiments, the vectors and compositions of the subject invention are locally injected into the targeted region of the eye, via an appropriate route such as subretinal, transscleral, or transcorneal administration.

The vectors and therapeutic compositions provided by the subject invention are typically administered to a mammal, particularly a human, dog or cat, any of which is intended to be encompassed by the term "patient" herein, in need of the prevention or treatment of pathological vascular proliferation. Pathological conditions involving vascular proliferation include, for example, tumor growth, age-related macular degeneration (AMD), diabetic retinopathy and retinopathy of prematurity (ROP).

In one method, the subject invention involves identifying an individual who has, or who is at risk for developing pathological vascularization and then providing that individual with a composition of the subject invention.

The terms "pharmaceutically acceptable carrier" or a "carrier" refer to any generally acceptable excipient or drug delivery device that is relatively inert and non-toxic. The agent can be administered with or without a carrier. When treating retinopathies, a preferred embodiment is to administer the agent to the retinal area or the vasculature around or leading to the retina. Suitable carriers (e.g., pharmaceutical carriers) include, but are not limited to sterile water, salt solutions (such as Ringer's solution), alcohols, polyethylene glycols, gelatin, carbohydrates such as lactose, amylose or starch, magnesium stearate, talc, silicic acid, viscous paraffin, fatty acid esters, hydroxymethylcellulose, polyvinyl pyrolidone, etc. Such preparations can be sterilized and, if desired, mixed with auxiliary agents, e.g., lubricants, preservatives, stabilizers, wetting agents, emulsifiers, salts for influencing osmotic pressure, buffers, coloring, and/or aromatic substances and the like which do not deleteriously react with the active compounds. They can also be combined where desired with other active substances, e.g., enzyme inhibitors, to reduce metabolic degradation. A carrier (e.g., a pharmaceutically acceptable carrier) is preferred, but not necessary to administer the agent.

Suitable non-toxic pharmaceutically acceptable carriers for use with the agent will be apparent to those skilled in the art of pharmaceutical formulation. See, for example, *Remington's Pharmaceutical Sciences*, seventeenth edition, ed. Alfonso R. Gennaro, Mack Publishing Company, Easton, Pa. (1985).

The therapeutic dosage range can be determined by one skilled in the art having the benefit of the current disclosure. Naturally, such therapeutic dosage ranges will vary with the size, species and physical condition of the patient, the severity of the patient's medical condition, the particular dosage form employed, the route of administration and the like.

According to the subject invention, the local ocular administration of active agent of the invention, and/or formulations thereof, attenuate ocular pathological disease processes. Thus, local ocular administration of the active agent of the invention, and/or formulations thereof, provides for an efficacious but safe controlled administration directly in the eye.

Ocular therapies, as described herein, provide significant advantages for treating neovascular ocular disease relative to current laser surgery treatment modalities including panretinal photocoagulation, which can be accompanied by extensive ocular tissue damage. In the examples of posterior neovascular ocular diseases, such as age related macular degeneration and diabetic retinopathy, target ocular pathologies and tissues for treatment are especially localized to the retinal, choroidal and corneal ocular compartments.

Preferably, the agent is administered locally to the eye, retinal area, choroid area or associated vasculature. The vectors and therapeutic composition can be administered in a single dose or in more than one dose over a period of time to confer the desired effect.

In a preferred embodiment, the agents of the subject invention can be formulated for parenteral administration. The preparation of an aqueous composition that contains one or more agents, such as a genetic construct of the subject invention, will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as freebase or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Compositions comprising the agents of the subject invention can be formulated into a composition in a neutral or salt form. Pharmaceutically acceptable salts include the acid addition salts and those formed with inorganic acids such as, for example, hydrochloric or phosphoric acids, or such organic acids as acetic, oxalic, tartaric, mandelic, and the like. Salts can also be derived from inorganic bases such as, for example, sodium, potassium, ammonium, calcium, or ferric hydroxides, and such organic bases as isopropylamine, trimethylamine, histidine, procaine and the like.

Sterile injectable solutions are prepared by incorporating the active compounds in the required amount in the appropriate solvent followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and freeze-drying techniques, which yield a powder of the active ingredient, plus any additional desired ingredient from a previously sterile-filtered solution thereof.

A further embodiment of the subject invention provides for the administration of agent compounds in combination with other pharmacological therapies. Combination therapies with other medicaments targeting similar or distinct disease mechanisms have advantages of greater efficacy and safety relative to respective monotherapies with either specific medicament.

In one embodiment, the composition is used to treat neovascular ocular disease by localized (for example, in ocular tissue) concurrent administration with other medicaments that act to block angiogenesis. Medicaments that can be concurrently administered with a peptide compound of the invention include, but are not limited to, vascular endothelial growth factor VEGF blockers (e.g. by VEGF neutralizing binding molecules such as MACUGEN® (Eyetech) and LUCENTIS® (ranibizumab, Genentech), Squalamine lactate (Genaera Corporation); and VEGF tyrosine kinase inhibition) for treating neovascular ocular disease (AMD and Diabetic Retinopathy) and glucocorticoids (e.g. Triamcinolone) for treating macular edema.

When administering more than one, the administration of the agents can occur simultaneously or sequentially in time. The agents can be administered before and after one another, or at the same time. The methods also include co-administration with other drugs that are used to treat retinopathy or other diseases described herein.

Materials and Methods

Cell Culture & Hypoxia Treatment

ARPE-19 (human RPE) cells were purchased from American Type Culture Collection (Manassas, Va.). Cell Cultures were propagated and maintained in Dulbecco's modified eagle medium (DMEM) or DMEM/F-12 (Cellgro-Mediatech, Herndon, Va.) and supplemented with 10% fetal bovine serum (HyClone, Logan, Utah) and 1% penicillin/streptomycin (Cellgro-Mediatech). All hypoxia experiments were performed using a Shel-Lab Bactron anaerobic glovebox chamber (Sheldon Manufacturing Inc, Cornelius, Oreg.).

Construction of Hypoxia Inducible Promoter (HRSE-6xHRE-RPE65)

The HRSE-6X-RPE65 promoter assembly has been described in Doughent et al. (2008). Briefly, the hypoxia responsive element (HRE) sequence is derived from the human phosphoglycerate kinase (PGK) gene in the sense orientation, 5'-TGT CAC GTC CTG CAC GAC GTA-3' (SEQ ID NO:2). The neuron restrictive silencer element (NRSE) sequence is derived from the human synapsin I gene in the sense orientation, 5'-TTC AGC ACC GCG GAC AGT GCC-3'(SEQ ID NO:3) (Brene et al. (2007)). The hypoxia regulated silencing element (HRSE) sequence was made by placing three copies of the NRSE sequence and three copies of the HRE in an alternating tandem order. The 6XHRE sequence was made by synthesizing six tandem copies of the HRE sequence into a single, 144 bp, double-stranded oligomer. The "6XHRE" sequence includes a Sac I restriction site at each terminus. The RPE65 promoter sequence is derived from the 5' upstream sequence (−325 to +52) of the RPE65 gene.

The RPE65, HSRE, and 6XHRE sequences were serially subcloned into a vector. Specifically, the native RPE65 promoter sequence was inserted into the vector at a multiple cloning site (MCS). Then the HRSE sequence was cloned into the MCS at a position just upstream of the RPE65 promoter to provide normoxic silencing. Additionally, the 6XHRE sequence was cloned into the MCS just downstream of the HRSE sequence. The 6XHRE sequence provides conditionally-enhanced expression of the transgene under hypoxia, during which the transcription factor HIF1 heterodimer translocates into the nucleus and binds HREs thereby upregulating transgene expression.

Hypoxia-Regulated, RPE-Specific Viral Vectors

Self-complimentary, hypoxia-regulated, and RPE-specific viral vectors were constructed to drive the expression of the therapeutic transgene-human endostatin gene. FIG. 1 illustrates the vector design.

Specifically, the human endostatin XVIII gene (along with SV40 poly A) was obtained by amplifying the human endostatin gene from the pBLAST42-hEndo XVIII expression vector (InvivoGen, San Diego, Calif.) using polymerase chain reaction (PCR). The scAAV2-CMV-hEndostatin vector ("scAAV2-CMV-Endo") was constructed by cloning the human endostatin XVIII gene is into a scAAV2 double stranded, self-complimentary adeno-associated viral vector. The scAAV2-HRES-6XHRE-RPE65-hEndostatin vector (abbreviated as "scAAV2-Regulated-Endostatin", "scAAV2-Reg-Endo", or "Reg-Endo") was constructed by replacing the CMV promoter sequence with the HRSE-6X-RPE65 promoter sequence in the scAAV2-CMV-hEndo vector. The scAAV2-Regulated-Endostatin vector as well as the scAAV2-CMV-Endo vector also contains a GFP sequence downstream of the human endostatin gene.

Proper placement and orientation of the promoter elements and the endostatin gene in both scAAV2-CMV-hEndo and scAAV2-Reg-Endo plasmids were confirmed by sequence analysis (CRC-DNA Sequencing Facility, University of Chicago, Chicago, Ill.) prior to production of viral stocks by the University of North Carolina's Vector Core facility (Chapel Hill, N.C.).

The scAAV2-HRES-6XHRE-RPE65-Endostatin vector produced a viral titer of $1.5 \times 10^{12}$ virus molecules/ml, while the scAAV2-CMV-Endostatin produced a viral titer of $2.0 \times 10^{12}$ virus molecules/ml.

The viral vectors were used in vitro rtPCR analysis of transgene expression and in vivo experiments. The scAAV2-CMV-Endostatin vector was diluted to producing a viral titer of $1.5 \times 10^{12}$ virus molecules/ml prior to use.

Reverse Transcription Polymerase Chain Reaction (rtPCR)

ARPE-19 cells were grown to confluence in tissue culture-treated six-well plates (Corning Life Sciences, Lowell, Mass.), and then transduced with 1 uL of scAAV-HRES-6XHRE-RPE65-Endostatin ($1.5 \times 10^{12}$ virus molecules/ml). The transduced cells and untransduced cells (negative control) were subjected to 24 hours of hypoxia or normoxia.

After incubation, cells were lysed, and total RNA was extracted and purified using an RNeasy Plus Mini kit (Qiagen, Valencia, Calif.). RNA concentration was determined by spectrophotometry. RNA was reverse-transcribed into cDNA using Superscript III Reverse Transcription Supermix (Invitrogen).

PCR was performed using 50 µl solution containing 10 ng cDNA, Platinum Taq polymerase (Invitrogen), dNTP, $MgCl_2$, and primers that target either the vector-derived endostatin sequence or the beta-actin sequence. The endostain primer pair amplifies a 682 base pair region of the vector-derived endostain gene that starts within the endostatin poly A region and ends within the GFP portion of the vector-derived endostain transcript, and has the following sequences: 5'-GAACAGCTTCATGACTGC-3' (SEQ ID NO:4) (Forward) and 5'-GGTGCAGATGAACTTCAG-3' (SEQ ID NO:5) (Reverse). The beta-actin primer pair amplifies a 367 base pair region within the beta-actin transcript, and has the following sequences 5' TCTACAATGAGCT-GCGTGTG 3' (SEQ ID NO:6) (Forward) and 5'-GGTGCA-GATGAACTTCAG-3' (SEQ ID NO:7) (Reverse). The beta-actin transcripts, which are endogenous and constitutively expressed, serve as the reaction and loading control.

After an initial incubation of 1 minute at 94° C., 35 cycles of PCR amplification (94° C. for 30 seconds, 49° C. for 30 seconds, 72° C. for 1 minute) were performed using a thermocycler (Eppendorf, Hauppauge, N.Y.). 25 µl of each amplified product was loaded into a 1% agarose gel (containing ethidium bromide) and resolved by electrophoresis. Bands were imaged using the Gel-Doc-it system and Lab-Works software (UVP, Upland, Calif.).

Animals

Female C57BL/J6 mice were used in the study. Because age is a contributing factor in AMD, all mice used for the AMD study were 7-9 months old (retired breeders). Mice were handled using procedures consistent with the ARVO Statement for the Use of Animals in Ophthalmic and Vision Research and approved by the FAU and University of Miami Institutional Animal Care and Use Committees (IACUC).

Subretinal Injections

Mouse pupils were dilated with 1% tropicamide, and the mice were dark-adapted prior to anesthetization. Anesthetization was performed by intraperitoneal injection of 80-100 mg/kg ketamine and 10 mg/kg of xylazine. After anesthetization, proparacaine hydrochloride local anesthesia was applied to each eye.

A pilot hole was made on the nasal cornea, just inside the pupil, with a 30 G½ disposable needle. A 33-gauge, blunt-ended needle mounted on a 10 ul Hamilton syringe was introduced through the corneal opening, carefully avoiding the lens, stopping at the anterior retina. One microliter of scAAV2-HRSE-6XHRE-RPE65-Endostatin, scAAV2-CMV-Endostatin (both $1.5 \times 10^{12}$ virus molecules/ml), or vehicle (PBS) was slowly injected into the subretinal space. One eye was injected with either scAAV2-CMV-GFP or scAAV2-HRES-6XHRE-RPE65-Endostatin, and the contralateral eye was injected with vehicle. Successful injections were confirmed upon fundus visualization of subretinal blebs, indicating retinal detachment. Such detachments are typically transient and are resolved within 24 hrs. Following injections, 1% atropine eye drops and neomycin/polymixin B/dexamethasone ophthalmic ointments were administered.

Mouse Model of Choroidal Neovascularization

The laser-induced murine model of CNV has been previously described in Kasman et al. (2008). One week following subretinal injection, pupils were dilated with 1% tropicamide, and mice were anesthetized with 80-100 mg/kg ketamine-10 mg/kg of xylazine by intraperitoneal injection. CNV was induced by irradiating mouse eye tissues with an argon 532 nm green diode laser (100 uM spot size, 150 mW intensity, 0.1 s duration-Nidek GYC-1000, Fremont, Calif.) mounted on a Haag-Streit slit lamp, using a coverslip as a contact lens.

Three lesions were made at 3, 6, and 9 o'clock positions between retinal vessels and 2-3 disc diameters away from the optic nerve. Formation of a bubble at the time of laser application indicated rupture of Bruch's membrane, which is an important factor for CNV induction. Only lesions that produce bubble(s) were assessed in this invention.

Histological Evaluation of Choroidal Neovascularization: RPE Flatmounts

Fourteen days post-laser treatment, mice were anesthetized with 80-100 mg/kg of ketamine and 10 mg/kg of xylazine. Vasculature was stained with 100 uL of 1 mg/mL fluorescein- or DyLight 594-conjugated *L. esculentum* (tomato) lectin (Vector Laboratories, Burlingame Calif.) in PBS via cardiac perfusion. Five minutes later, the mice were sacrificed by 100% $CO_2$ and the eyes were enucleated and placed in 1×PBS. A hole was made in the cornea prior to fixing in 4% PFA for one hour. The anterior chamber, lens and cornea were dissected out, and the neurosensory retina was carefully removed from the RPE layer. The remaining RPE, choroid, sclera complex was flatmounted on a slide by making 3-4 radial incisions, being careful to avoid any lesions. The retinal flatmounts were coverslipped using Vectashield hard-set mounting media with DAPI counterstain (Vector Laboratories, Burlingame, Calif.).

Retinal flatmounts were observed using a Leica SP5 confocal microscope (Leica Microsystems, Wetzlar, Germany) with a 20× objective under FITC (excitation at 488 nm and emission at 535 nm) and DAPI (excitation at 350 nm and emission at 470 nm) filters. Compressed 20 um Z-stack images (1 um/frame) were obtained for each lesion using Leica's LAS software (Leica Microsystems). CNV area for each lesion was quantified using Image J (National Institute of Health, Bethesda, Md.).

The initial number of CNV lesions associated with bubble formation upon laser application was 331 (138 vehicle treated, 169 Reg-Endo treated, and 24 CMV-Endo treatment). The following exclusion and inclusion criteria for CNV lesions and area measurements were developed and implemented by an investigator masked with respect to treatment groups. CNV lesions associated with retinal bleeding from the site of laser application were excluded; this is indicative of the laser rupturing a minor retinal vessel (since major vessels are easily seen and avoided) and typically caused fusion of the ruptured retinal vessel(s) with the underlying CNV growth. Additionally, lesions that had various discrepancies with flatmount preparation (i.e. adherence to neurosensory retina) and complications that interfered with microscopic documentation (i.e. weak/blurred lectin staining and inadequate imaging) were excluded.

The remaining lesions were included into the raw data set, which was composed of 58 vehicle treated, 78 Reg-Endo treated, and 19 CMV-Endo treated lesions stored as 20× compressed Z-stack confocal micrographs. After 3 independent measurements of CNV area were made, for each lesion in the raw data set, the final exclusions were made to create the final data set, which was used to calculate the statistical significance between treatment groups. The final data set excluded coalesced lesions that had no discernable boundaries and lesions that contained vessels or portions of vessels from the neurosensory retina. Also, outliers were identified, and eliminated if the percentage of standard deviation for the 3 area measurements was greater than 15% of their average.

The final data set included 53 vehicle treated, 53 Reg-Endo treated, and 17 CMV-Endo treated lesions. The average of the 3 independent CNV area measurements for each lesion was used for data analysis.

Statistical analysis was made using a student's paired t test (2-tailed), for either AAV2-CMV-Endostatin or AAV2-HRSE-HRE-RPE65-Endostatin versus vehicle control. Mean CNV areas were also compared between the eyes that were injected with AAV2-HRES-6XHRE-RPE65-Endostatin and the vehicle injected eyes that had two or more quantifiable lesions for each eye.

Histological Evaluation of Choroidal Neovascularization: Cryosections

Mice were subretinally injected with AAV2-HRSE-6XHRE-RPE65-Endostatin, scAAV2-CMV-Endostatin, or vehicle. CNV was induced 1 week following subretinal injection. Eyes were harvested from mice at 3 days post-laser injury. Enucleated eyes were fixed in 4% paraformaldehyde in PBS for 1 hr, cryoprotected overnight in 30% sucrose in PBS, embedded in Tissue-Tek optimal cutting temperature (OCT), snap frozen in liquid nitrogen, and stored at −80° C.

8 µm serial cryosections were mounted on charged slides and briefly washed in PBS. Tissues were then blocked for 2 hrs with PBS containing 5% horse serum and 0.1% Triton X-100. Sections were incubated in primary antibody (goat anti-human endostatin; 1:100 in blocking buffer, R&D Systems, Minneapolis, Minn.) overnight at 4° C. Then, the sections were washed with PBS/0.1% Triton X-100, and incubated in donkey anti-goat-Alexa-488 secondary antibody (1:1000 in PBS, Molecular Probes, Eugene, Oreg.) for two hours at room temperature. The sections were then washed with PBS/0.1% Triton X-100, and the slides were air-dried prior to coverslipping with Vectashield Hard Set Mounting Medium with DAPI (Vector Laboratories, Inc., Burlingame, Calif.).

The sections were imaged with a Nikon Eclipse TE2000-S inverted fluorescent microscope (Nikon Instruments Inc., Melville, N.Y.) using FITC and DAPI filters. All images were captured at 10× and 20× under the same conditions using Nikon's NIS Imaging software.

EXAMPLES

Following are examples that illustrate embodiments for practicing the invention. The examples should not be construed as limiting.

Example 1

Hypoxia-Induced Production of Endostatin Transcripts

This Example shows that the scAAV-HRES-6XHRE-RPE65-Endostatin viral vector produces viable endostatin transcripts in RPE cells under hypoxia but not under normoxia.

FIG. 1 illustrates the design of viral vectors used in the Examples. ARPE-19 cells were transduced with the scAAV-HRES-6XHRE-RPE65-endostatin ("Reg-Endo") vector, and the transduced cells were exposed to 24 hours of hypoxia or normoxia.

RtPCR was performed using primers that selectively amplify a 682 bp region of cDNA of the Reg-Endo vector. The amplified region begins within the endostatin poly adenylation signal and terminates within the GFP sequence. The presence of the GFP sequence, which is not endogenous to ARPE-19 cells, can be detected rtPCR; Cells that produce transcripts containing the GFP sequence contain the Reg-Endo vector.

Figure 2:
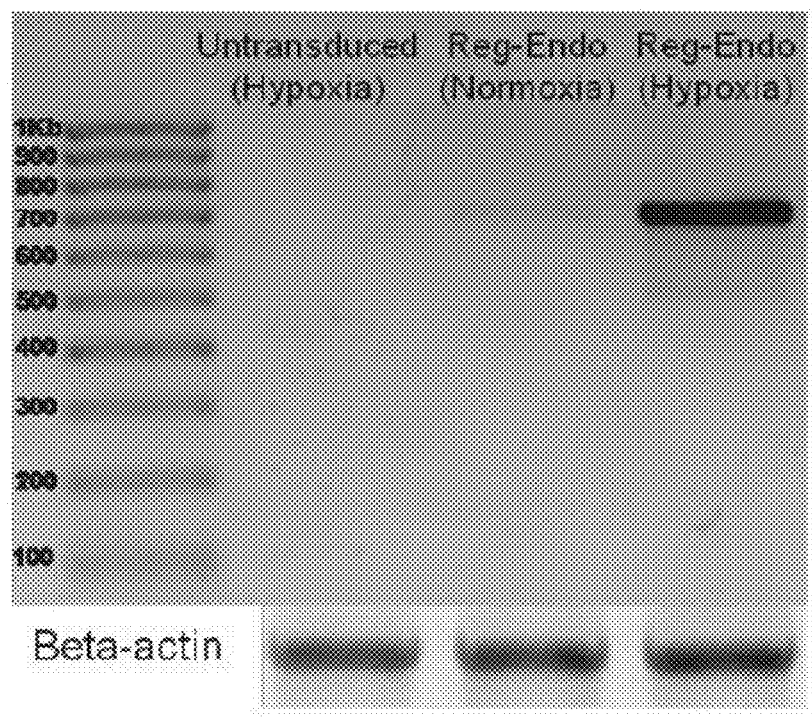
FIG. 2 shows rtPCR analysis of virus-derived hrEndostatin mRNA transcripts from ARPE-19 cells transduced with scAAV-HRSE-6XHRE-RPE65 and subjected to either 24 hours of hypoxia (1% $O_2$) or normoxia (21% $O_2$). RtPCR of mRNA from untransduced ARPE-19 cells, exposed to the same hypoxic and normoxic conditions, was used to ensure that endogenous transcripts were not inadvertently amplified. A 682 bp band indicates presence of viral transcripts. The results indicate minimal viral expression in normoxia, along with a strong hypoxic-induction of viral transcripts. Untransduced cells lacked the presence of virus-derived endostatin transcripts in hypoxia.

The results show that there is very minimal expression of virus-derived endostatin mRNA in normoxia, and a high level of endostain expression following hypoxic exposure (FIG. 2). The PCR products are of the same size as products amplified from both the purified Reg-Endo plasmid and the denatured Reg-Endo virus.

In addition, rtPCR was performed using mRNA isolated from untransduced ARPE-19 cells. No virus-derived endostatin transcripts were detected from in cells placed under hypoxia (FIG. 2) as well as normoxia.

Example 2

Reduction of Laser-Induced CNV by Hypoxia-Regulated, RPE-Specific Endostatin Gene Therapy This Example shows that hypoxia-regulated, RPE-specific endostatin gene therapy effectively inhibits chorodial neovascularization (CNV), and can be used to prevent and treat ocular neovascular diseases such as age-related muscular degeneration (AMD).

Briefly, 1 uL ($1.5 \times 10^9$ virus molecules) of the AAV2-Reg-Endo vector, the AAV2-CMV-Endo vector, or vehicle (VC) was subretinally injected into the subretinal space of C57BL/J6 mice via the trans-corneal route. Nearly 100% of RPE transduction was observed three weeks after injection. A scAAV2-CMV-GFP vector was used to confirm transduction efficiency prior to the use of the endostatin vectors.

One week following subretinal injection, mouse eye tissues are irradiated with a laser beam of 532 nm (100 μm/150 mW) to induce CNV by laser rupture of Bruch's membrane. The laser-induced murine model of CNV is an art-recognized animal model of AMD.

Confocal microscopy of RPE flatmounts was performed two weeks following laser injury. The two-week time period provided sufficient time for CNV development and coincided with the three week period for maximal vector expression.

The mean area of laser-induced CNV lesions following subretinal injection of scAAV2-HRES-6XHRE-RPE65-Endostatin was compared to that of vehicle-injected, and scAAV2-CMV-Endostatin-injected retinas. The CMV promoter is not cell-specific and is considered one of the most constitutively active promoters used in gene therapy; therefore, the level of endostain production in the eyes injected with the scAAV2-CMV-Endostatin vector can indicate whether the hypoxia-regulated, RPE-specific promoter produce sufficient amount of endostatin to reduce CNV lesion area. In addition, the scAAV2-CMV-Endostatin vector, which contains the ubiquitously-expressed CMV promoter, would indicate whether RPE is an appropriate area of the retina for endostatin expression at a level that is effective for reduction of CNV growth.

Figure 3:
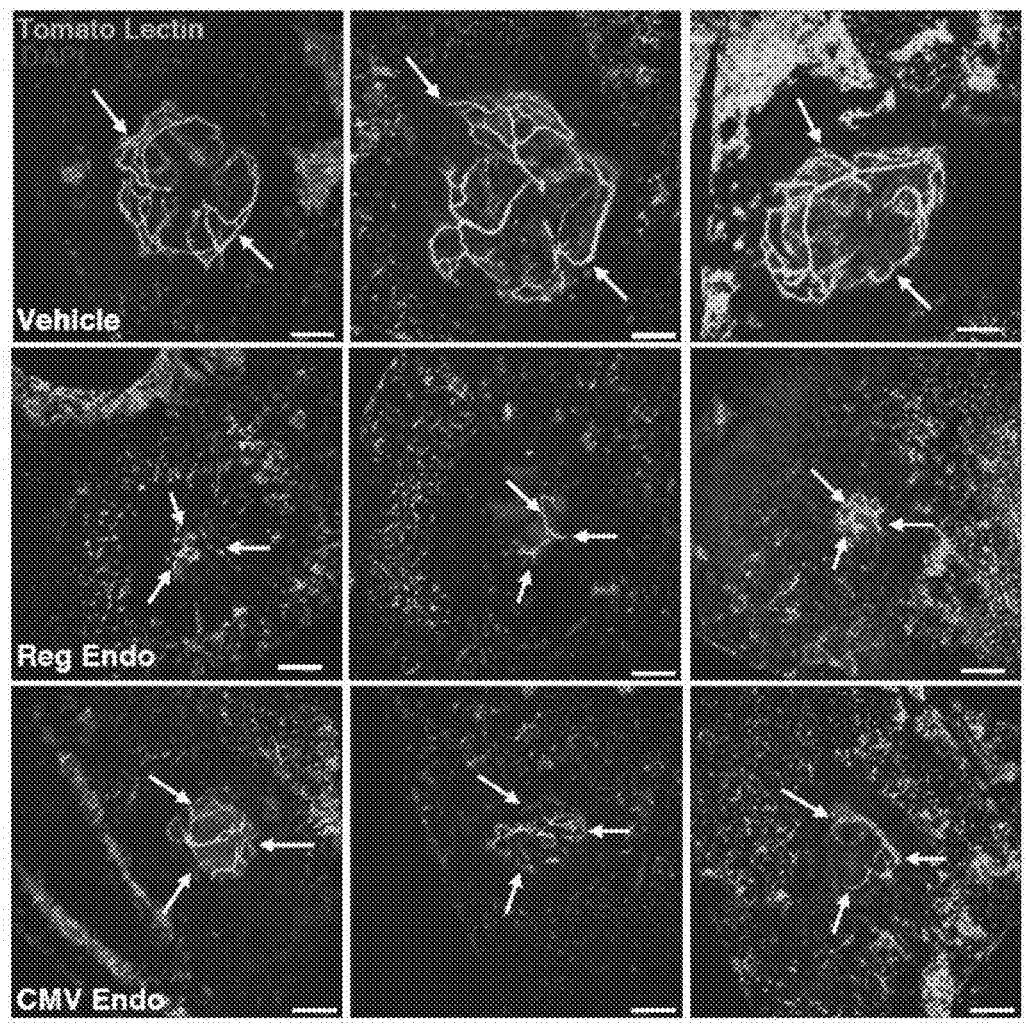
FIG. 3 shows representative confocal micrographs of CNV lesions from RPE flatmounts. The top row shows CNV lesions of mice subretinally injected with vehicle control. The middle row shows CNV lesions of mice subretinally injected with scAAV2-HRES-HRE-RPE65-Endostatin (Reg Endo). The bottom row shows CNV lesions of mice subretinally injected with scAAV2-CMV-Endostatin. Arrows indicate CNV lesion boundary. Green=fluoroscein-conjugated tomato lectin perfused vasculature; blue=DAPI nuclear stain. Scalebars=100 um.

FIG. 3 shows representative confocal micrographs of CNV lesions of the eyes injected with the AAV2-Reg-Endo vector, the AAV2-CMV-Endo vector, or vehicle (VC). The lesions in the vehicle-injected eyes were visibly much larger, with more tortuous neovascular growth (green "vessels" in FIG. 3) than the endostatin vector-injected group. Subretinal administration of AAV2-HRES-6XHRE-RPE65-Endostatin resulted in a remarkable, 80% reduction in mean CNV area, compared to lesions from vehicle injected eyes (51 435±3 535 um$^2$ vs. 257 701±15 310 um$^2$; P<0.001; FIG. 4A). Subretinal injection of AAV2-CMV-Endostatin reduced mean CNV area by 75.8%, compared to lesions from vehicle injected eyes (62 345±9 354 um$^2$ vs. 257 701±15 310 um$^2$; P<0.001).

This Example also compares mean CNV areas of lesions in the eyes injected with the scAAV2-HRES-6XHRE-RPE65-Endostatin vector with that of the vehicle injected eyes that had at least two measurable lesions per eye (FIGS. 4B & C). This comparison eliminates variability between animals, thereby making a more accurate assessment of lesion areas between treatment groups. Mean CNV areas in the Regulated-Endostatin treated eyes were at least 76% smaller than that of the vehicle-injected contralateral eyes (56 332±19 991 um$^2$ vs. 231 275±84 548 um$^2$; P<0.001).

Figure 5:
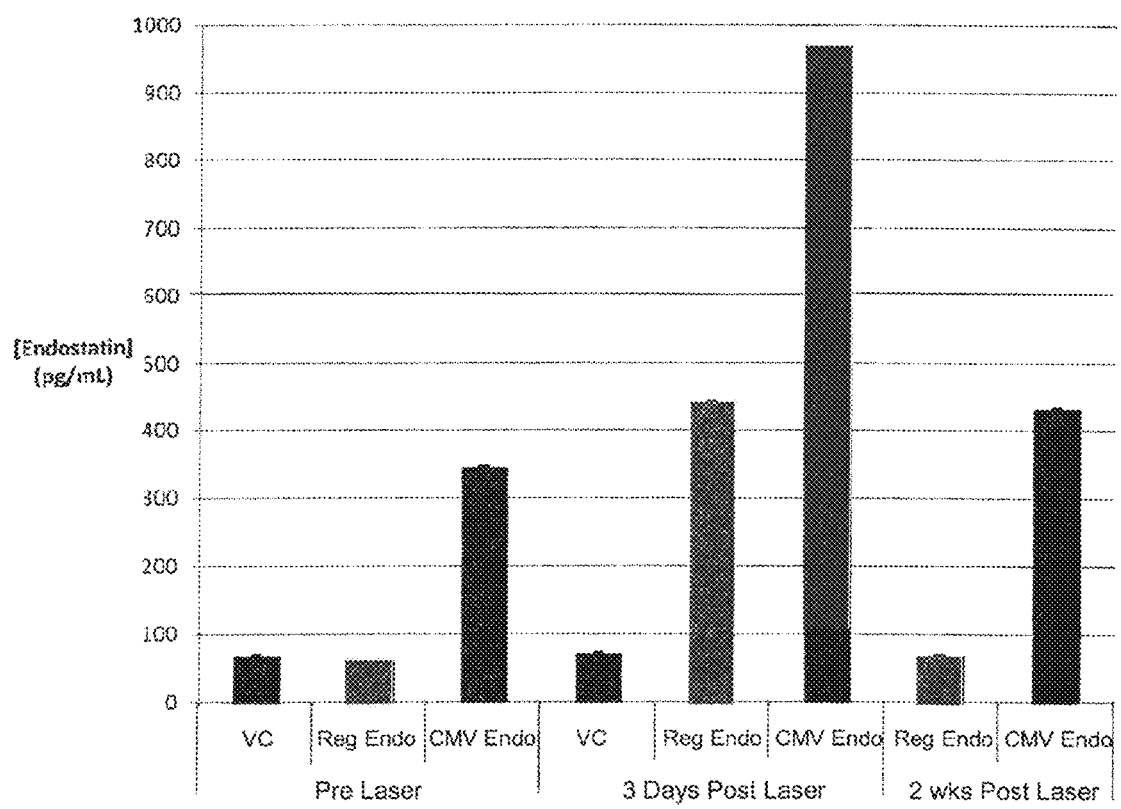
FIG. 5 shows human endostatin concentrations measured by ELISA. Mice are subretinally injected with the AAV2-Reg-Endo vector, the AAV2-CMV-Endo vector, or vehicle (VC). Each sample represents 4 homogenized posterior eyecups pooled for each of the 3 treatment groups at 3 time points: pre-laser (5 days post-injection), 3 days post-laser, and 2 weeks post-laser. The results show that there is a conditional silencing of the reg-endo vector before laser injury, then enhanced activation subsequent to laser injury, and a return to baseline two weeks post-laser injury. Endostatin concentrations in mice treated with the CMV-endo vector are elevated prior to laser injury, and remain elevated through the 2 week post-laser time point.

Each sample of FIG. 5 represents 4 homogenized posterior eyecups pooled for each of the 3 treatment groups at 3 time points: pre-laser (5 days post-injection), 3 days post-laser, and 2 weeks post-laser. Endostatin expression from the hypoxia regulated vector is initiated by laser injury to the retina, and is reduced 2 weeks following laser induction (FIG. 5). Specifically, FIG. 5 shows that there is conditional silencing of the Reg-Endo vector before laser injury, then enhanced activation subsequent to laser injury, and a return to baseline 2 weeks post-laser injury.

In comparison, for mice injected with the CMV-Endo vector, endostatin concentrations are elevated prior to laser injury and remain elevated through the two-week post-laser time point. Constitutive endostatin expression in retinal tissues can produce detrimental effects to non-pathological tissues. For example, in non-diseased regions of the eye, elevated endostatin could have a range of effects that may alter endogenous cell-to-cell communication and interactions.

Figure 6:
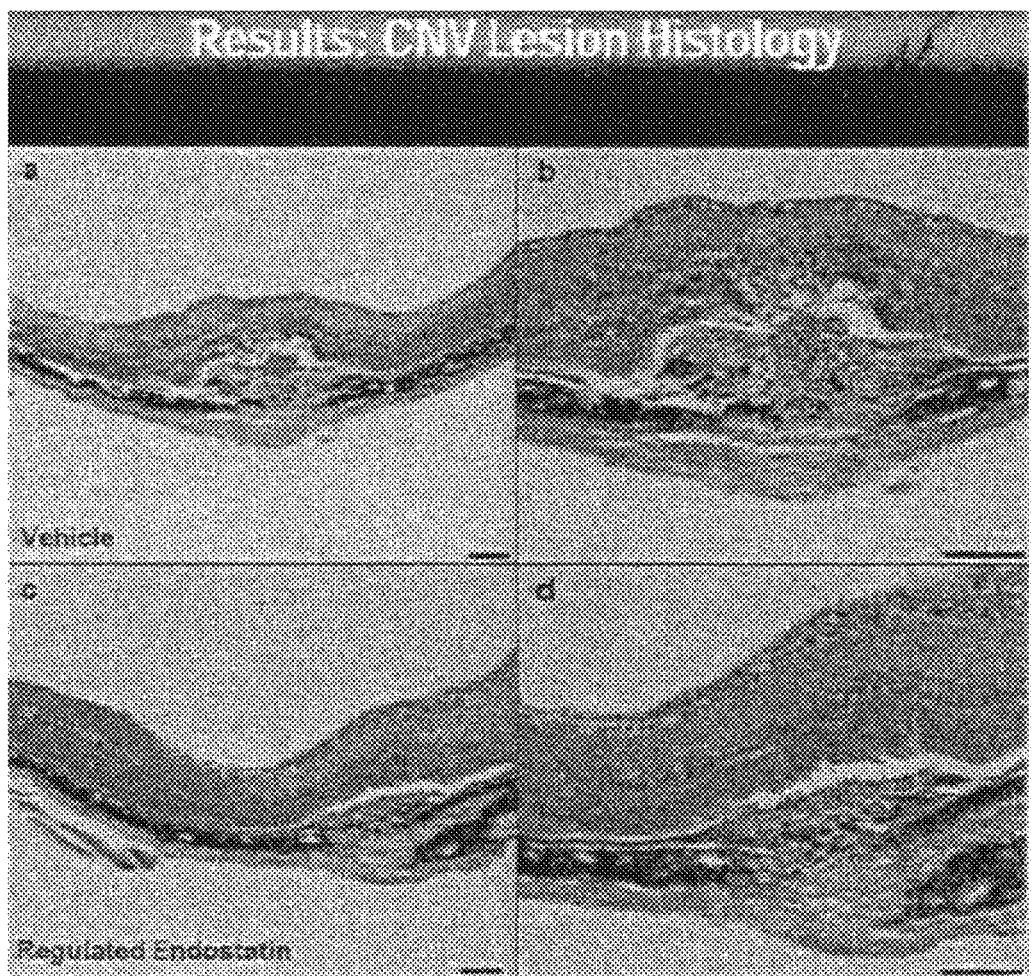
FIG. 6 shows CNV lesion histology light micrographs of CNV lesions of the mice 3 days post-laser injury. Images are derived from mice injected with the regulated-endostatin injected vector, 6 months post-injection (a & b), and contralateral vehicle control injected eyes (c & d) from the same mouse. Hematoxalin & Eosin; b & d are higher magnification of a & c. Scale bars=100 μm.

The CNV lesion histology light micrographs (FIG. 6) also show that the hypoxia-regulated, RPE-specific endostatin (scAAV2-HRES-6XHRE-RPE65-Endostatin) gene therapy significantly reduced CNV lesion size.

Example 3

Immunohistochemical Localization of Regulated Expression of Endostatin Protein

Figure 7:
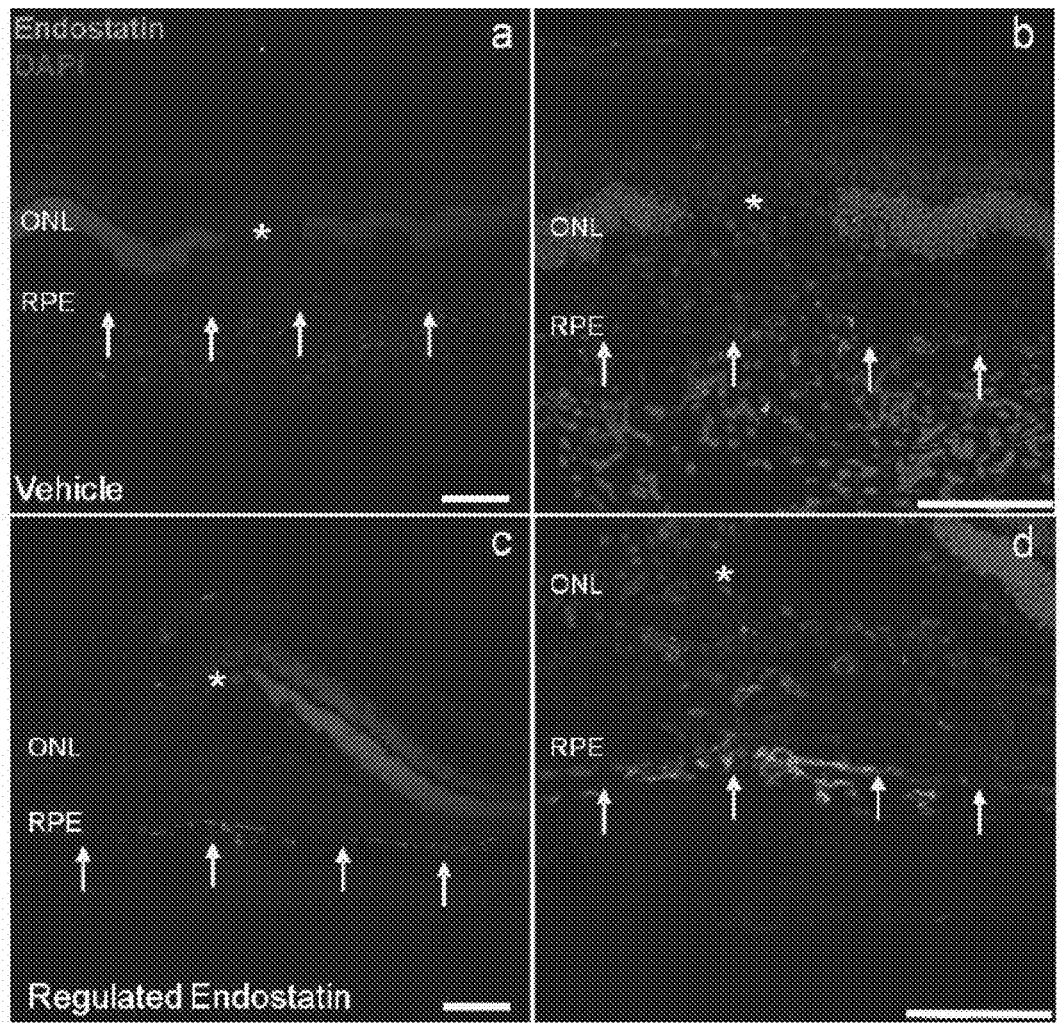
FIG. 7 shows immunohistochemical localization of human endostatin (green) in cryosections through CNV lesions in eyes injected with vehicle (a, b) or the regulated endostatin vector (c,d). The eyes were harvested 3 days post-laser injury. b & d are higher magnification images of a & c. Arrows indicate RPE/Choroid interface. Asterisk indicates center of lesion. Scale bars=100 μm; ONL, outer nuclear layer; RPE, retinal pigment epithelium.

Immunohistochemistry of CNV lesions obtained 3 days post-laser injury confirmed that expression of human endostatin protein is focally elevated within the area of laser damage (FIG. 7). Endostatin expression was localized at the RPE/choroid interface, which indicates its expression and secretion from the basal side RPE subsequent to laser-induced inflammation and hypoxia. No detectable level of endostatin was observed in unlasered eyes treated with scAAV2-Regulated-Endostatin.

All references, including publications, patent applications and patents, cited herein are hereby incorporated by reference to the same extent as if each reference was individually and specifically indicated to be incorporated by reference and was set forth in its entirety herein.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of" or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

It should be understood that the examples and embodiments described herein are for illustrative purposes only and that various modifications or changes in light thereof will be suggested to persons skilled in the art and are to be included within the spirit and purview of this application.

REFERENCES

Bainbridge, J. W., A. Mistry, et al. (2003). "Hypoxia-regulated transgene expression in experimental retinal and choroidal neovascularization." Gene Ther 10(12): 1049-1054.

Balaggan, K. S., K. Binley, et al. (2006). "EIAV vector-mediated delivery of endostatin or angiostatin inhibits angiogenesis and vascular hyperpermeability in experimental CNV." Gene Ther 13(15): 1153-1165.

Cideciyan, A. V., W. W. Hauswirth, et al. (2009). "Human RPE65 gene therapy for Leber congenital amaurosis: persistence of early visual improvements and safety at 1 year." Hum Gene Ther 20(9): 999-1004.

Dougherty, C. J., Smith, G. W., Prentice, H. M., Dorey, C. K., Webster, K. A. and Blanks, J. C. Robust Hypoxia-Selective Regulation of an RPE-Specific AAV Vector. Molecular Vision (2008).

Kachi, S., K. Binley, et al. (2009). "Equine infectious anemia viral vector-mediated codelivery of endostatin and angiostatin driven by retinal pigmented epithelium-specific VMD2 promoter inhibits choroidal neovascularization." Hum Gene Ther 20(1): 31-39.

Mori, K., A. Ando, et al. (2001). "Inhibition of choroidal neovascularization by intravenous injection of adenoviral vectors expressing secretable endostatin." Am J Pathol 159(1): 313-320.

Ruan, H., H. Su, et al. (2001). "A hypoxia-regulated adeno-associated virus vector for cancer-specific gene therapy." Neoplasia 3(3): 255-263.

Tang, Y. L., Y. Tang, et al. (2005). "A hypoxia-inducible vigilant vector system for activating therapeutic genes in ischemic." Gene Ther 12(15): 1163-1170.

Boulanger A, Liu S, Henningsgaard A A, Yu S, Redmond T M. The upstream region of the Rpe65 gene confers retinal pigment epithelium-specific expression in vivo and in vitro and contains critical octamer and E-box binding sites. *J Biol Chem* 2000; 275(40): 31274-82.

Brene S, Messer C, Okado H, Hartley M, Heinemann S F, Nestler E J. Regulation of GluR2 promoter activity by neurotrophic factors via a neuron-restrictive silencer element. *Eur J Neurosci* 2000; 12(5): 1525-33.

Kong F, Li W, Li X, Zheng Q, Dai X, Zhou X et al. Self-complementary AAV5 vector facilitates quicker transgene expression in photoreceptor and retinal pigment epithelial cells of normal mouse. *Exp Eye Res* 2010; 90(5): 546-54.

We claim:

1. A method of reducing or preventing ocular neovascularization in a subject, wherein the method comprises administering, into one or more target ocular tissues of the subject, said target ocular tissues selected from the group consisting of the retinal, choroidal and corneal ocular compartments, an expression vector comprising a transgene encoding a therapeutic molecule, wherein the transgene is operably linked to an ocular-specific promoter and becomes hypoxia-responsive when said ocular-specific promoter is placed under the control of a hypoxia-responsive element and selectively drives gene expression in retinal cells, retinal pigment epithelial cells, Muller cells, choroid cells and combinations thereof;

wherein said hypoxia responsive element is a hypoxia regulated silencing element (HRSE) including at least one hypoxia responsive element (HRE) sequence which upregulates gene expression under hypoxia or inflammation and at least one neuron-restrictive silencer element (NRSE) sequence which silences gene expression under normoxia, wherein the ocular-specific promoter selectively drives gene expression in the ocular tissue having, or at risk of developing, neovascularization, wherein the hypoxia-responsive element upregulates gene expression under hypoxia but not under normoxia, whereby ocular neovascularization is reduced or prevented.

2. The method of claim 1, wherein the HRSE comprises at least three copies of the hypoxia response element (HRE) sequence.

3. The method of claim 1, wherein the HRE sequence comprises SEQ ID NO:1 or SEQ ID NO:2.

4. The method of claim 1, wherein the HRSE comprises at least two copies of a hypoxia response element (HRE) sequence and at least two copies of a neuron-restrictive silencer element (NRSE) sequence, wherein the HRE and the NRSE are placed in alternating tandem order.

5. The method of claim 1, wherein the ocular-specific promoter selectively drives gene expression in retinal epithelial cells.

6. The method of claim 1, wherein the ocular-specific promoter is a RPE65 promoter sequence.

7. The method of claim 1, wherein the expression vector comprises, in the 5' to 3' direction, an aerobic silencer comprising at least two copies of a hypoxia response element (HRE) sequence and at least two copies of a neuron-restrictive silencer element (NRSE) sequence, wherein the HRE and the NRSE are placed in alternating tandem order;
- at least three copies of the hypoxia response element (HRE) sequence;
- a RPE65 promoter sequence; and
- a transgene gene encoding endostatin.

8. The method of claim 1, wherein the therapeutic molecule is an angiogenesis inhibitor.

9. The method of claim 8, wherein the angiogenesis inhibitor is selected from the group consisting of endostatin, a fibroblast growth factor (FGF) receptor, a VEGF receptor, angiostatin, pigment epithelium-derved factor (PEDF), platelet factor 4 (PF-4), and combinations thereof.

10. The method of claim 9, wherein the angiogenesis inhibitor is endostatin.

11. The method of claim 1, wherein the expression vector is an AAV vector.

12. The method of claim 1, used to prevent or treat choroidal neovascularization.

13. The method of claim 1, used to prevent or treat neovascularization in age-related macular degeneration, histoplasmosis, myopic degeneration, choroidal rupture, photocoagulation, choroidal hemangioma, choroidal nonperfusion, choroidal osteomas, choroideremia, retinal detachment, neovascularization at ora *serrata*, punctate inner choroidopathy, radiation retinopathy, and/or retinal cryoinjury.

14. The method of claim 1, used to prevent or treat retinal and/or corneal neovascularization.

15. The method of claim 1, wherein the expression vector is administered via subretinal injection.

\* \* \* \* \*

SEQUENCE LISTING

```
<160> NUMBER OF SEQ ID NOS: 7

<210> SEQ ID NO 1
<211> LENGTH: 6
<212> TYPE: DNA
<213> ORGANISM: Artificial Sequence
<220> FEATURE:
<223> OTHER INFORMATION: hypoxia responsive element (HRE)
<220> FEATURE:
<221> NAME/KEY: misc_feature
<222> LOCATION: (1)..(1)
<223> OTHER INFORMATION: n is a or g
<220> FEATURE:
<221> NAME/KEY: misc_feature
<222> LOCATION: (5)..(5)
<223> OTHER INFORMATION: n is g or c

<400> SEQUENCE: 1 ncgtnc                                                               6

<210> SEQ ID NO 2
<211> LENGTH: 21
<212> TYPE: DNA
<213> ORGANISM: Artificial Sequence
<220> FEATURE:
<223> OTHER INFORMATION: hypoxia responsive element (HRE)

<400> SEQUENCE: 2
tgtcacgtcc tgcacgacgt a                                             21

<210> SEQ ID NO 3
<211> LENGTH: 21
<212> TYPE: DNA
<213> ORGANISM: Artificial Sequence
<220> FEATURE:
<223> OTHER INFORMATION: neuron restrictive silencer element (NRSE)
```

```
<400> SEQUENCE: 3
ttcagcaccg cggacagtgc c                                              21

<210> SEQ ID NO 4
<211> LENGTH: 18
<212> TYPE: DNA
<213> ORGANISM: Artificial Sequence
<220> FEATURE:
<223> OTHER INFORMATION: primer sequence

<400> SEQUENCE: 4
gaacagcttc atgactgc                                                  18

<210> SEQ ID NO 5
<211> LENGTH: 18
<212> TYPE: DNA
<213> ORGANISM: Artificial Sequence
<220> FEATURE:
<223> OTHER INFORMATION: primer sequence

<400> SEQUENCE: 5
ggtgcagatg aacttcag                                                  18

<210> SEQ ID NO 6
<211> LENGTH: 20
<212> TYPE: DNA
<213> ORGANISM: Artificial Sequence
<220> FEATURE:
<223> OTHER INFORMATION: primer sequence

<400> SEQUENCE: 6
tctacaatga gctgcgtgtg                                                20

<210> SEQ ID NO 7
<211> LENGTH: 18
<212> TYPE: DNA
<213> ORGANISM: Artificial Sequence
<220> FEATURE:
<223> OTHER INFORMATION: primer sequence

<400> SEQUENCE: 7
ggtgcagatg aacttcag                                                  18
```